United States Patent

Coy

[19]

[11] Patent Number: 6,100,083
[45] Date of Patent: Aug. 8, 2000

[54] ANAEROBIC CHAMBER WITH COLLAPSIBLE DIAPHRAGM

[75] Inventor: Richard A. Coy, Grass Lake, Mich.

[73] Assignee: Coy Laboratory Products, Inc., Grass Lake, Mich.

[21] Appl. No.: 09/270,348

[22] Filed: Mar. 16, 1999

[51] Int. Cl.[7] .................................................... C12M 1/00
[52] U.S. Cl. ..................... 435/303.2; 312/1; 422/104; 600/22; 435/303.1
[58] Field of Search ................................. 312/1; 422/104; 600/22; 435/303.1, 303.2

[56] References Cited

U.S. PATENT DOCUMENTS 4,111,753  9/1978  Folsom et al. .......................... 435/303.2
4,892,830  1/1990  Findley et al. ......................... 435/303.1
5,861,305  1/1999  Silley et al. ........................... 435/286.6

Primary Examiner—David A. Redding
Attorney, Agent, or Firm—Harness, Dickey & Pierce P.L.C.

[57] ABSTRACT

An enclosure defining an anaerobic chamber for confining an anaerobic atmosphere, cuff and sleeve assemblies mounted on the enclosure in an airtight relation to the chamber so as to enable a scientist to insert his/her arms into said cuff and sleeve assemblies in an airtight manner so that his/her hands can be projected into the chamber without allowing oxygen into the chamber thereby offering the scientist the glove-free ability to handle and inspect samples in the chamber and thereby improve tactile efficiency, and an expandable and collapsible diaphragm mounted on said enclosure so as to communicate with said chamber so as to provide a continuous visual signal as to the condition of the atmosphere in the chamber, collapse of the diaphragm indicating that oxygen is leaking into the chamber.

1 Claim, 2 Drawing Sheets

ANAEROBIC CHAMBER WITH COLLAPSIBLE DIAPHRAGM

BACKGROUND AND SUMMARY OF THE INVENTION

This invention relates generally to anaerobic chambers for confining an anaerobic atmosphere and more particularly to a gloveless anaerobic chamber that offers the operator a convenient glove-free ability to handle and inspect samples.

A typical use for an anaerobic chamber is in the culturing of strict anaerobes. Various apparatus and pieces of equipment are contained within the enclosure for use in anaerobe culture. The enclosure is typically transparent, clear vinyl plastic for example, and work gloves for use by attending personnel are mounted in the wall of the enclosure. The personnel perform various work tasks within the enclosure via use of the flexible work gloves.

However, it is sometimes desirable for personnel performing particular work tasks within the enclosure to perform the tasks with their bare hands.

It is known to provide glove-less systems for anaerobic chambers. However, the presence of oxygen in the anaerobic chamber, even in minute amounts can be disruptive to the anaerobic culturing process. The likelihood of leaks of oxygen into the anaerobic chamber is always a possibility when using sleeves on the operators arms in a glove-free system.

Accordingly, there is a real need for providing a continuous visual signal in a glove-free system so that the operator is instantly aware of the presence of oxygen in the chamber before the culturing process has been disrupted.

It is an object, therefore of this invention, to provide an enclosure for a glove-free system that provides a continuous visual signal as to the condition of the atmosphere in the chamber.

In the anaerobic chamber of this invention, an enclosure is provided that has side-by-side access openings for cuff and sleeve assemblies through which the operator can gain access to the processes in the chamber and an expandable diaphragm is mounted on the enclosure so as to provide access to the anaerobic chamber, the diaphragm being normally in a bulging out mode indicating that the chamber is free of oxygen, but when the diaphragm collapses when there is a leakage of oxygen into the chamber. The operator, when performing tasks with his bare hands inside the enclosure, has the diaphragm at substantially at eye level thereby providing an instantaneous recognizable signal that there is a leak in the system thereby enabling the operator to plug the leak before substantial damages have been incurred.

Further, the glove-free ability to handle and inspect samples, as in this invention, permits the operators arms to enter the chamber without compromising the chamber atmosphere. Tactile efficiency is thereby improved.

The foregoing features, advantages and benefits of the present invention, along with additional ones, will be seen in the ensuing description and claims which should be considered in conjunction with the accompanying drawings wherein like reference numerals designate like parts. The drawings disclose presently preferred embodiments of the invention in accordance with the best mode presently contemplated for carrying out the invention.

DESCRIPTION OF THE PREFERRED EMBODIMENT

Figure 1:
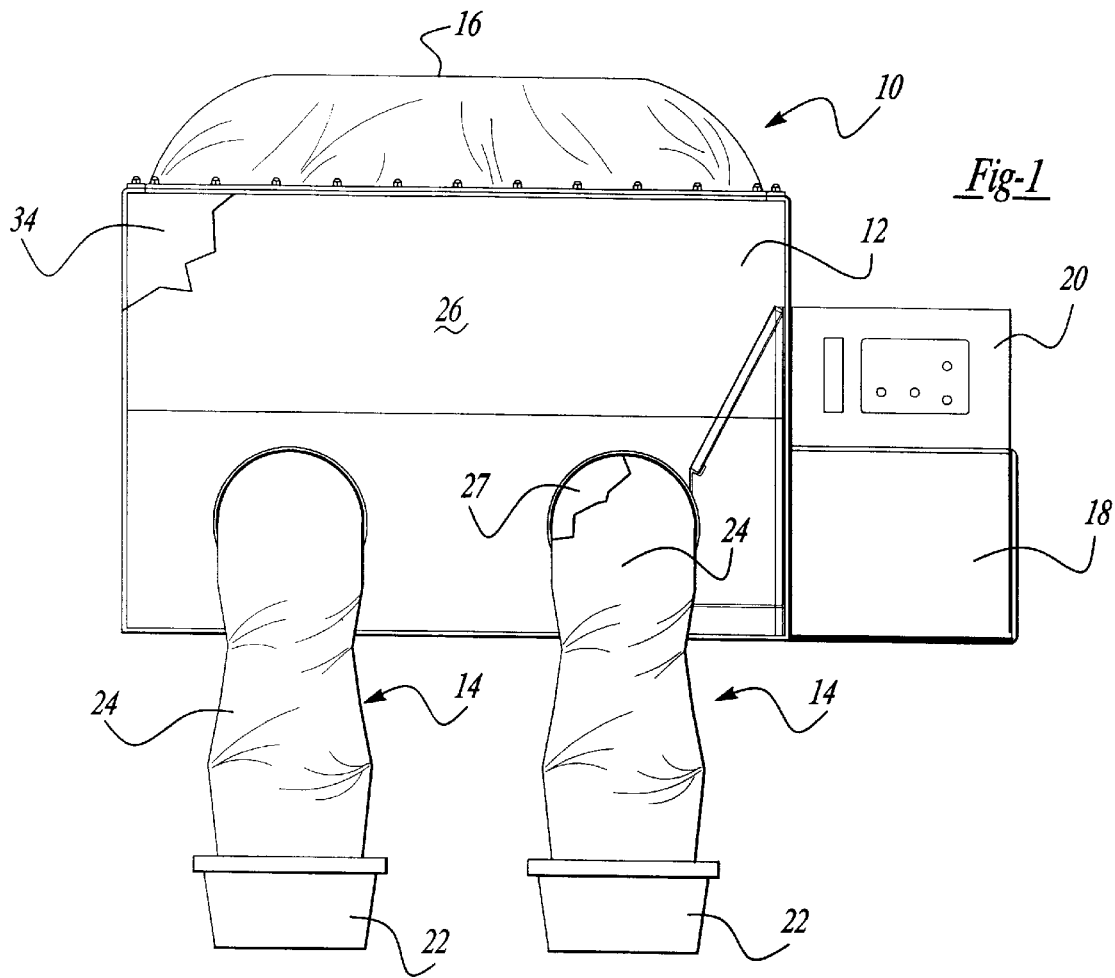
FIG. 1 is a front elevational view of the gloveless anaerobic enclosure of this invention showing the portions of the enclosure where the cuff and sleeve assemblies are joined to the enclosure and showing the location of the diaphragm which collapses to indicate an oxygen leak.

With reference to the drawing, the gloveless anaerobic chamber 10 is shown in FIG. 1 as including an enclosure 12, cuff and sleeve assemblies 14, a collapsible diaphragm 16, an airlock enclosure 18 which communicates with the anaerobic chamber inside the enclosure 12 through a door in the side of the enclosure 12 (not shown) and a cabinet 20 for various valves and gauges, (not shown).

Each of the assemblies 14 includes a cuff 22 made of a flexible material such as rubber or rubber-like plastic that will conform to the wrist of an operator so that the wrist and the cuff 22 are squeezed tightly enough with respect to each other to prevent oxygen leaks through the cuff. Each sleeve 24 is secured to a cuff 22 at one end and at the other end to the front wall 26 at a position around an opening 27. The sleeve 24 is formed of a material having high tensile strength and flexibility likewise for the purpose of avoiding leaks of oxygen through the sleeves 24.

Figure 2:
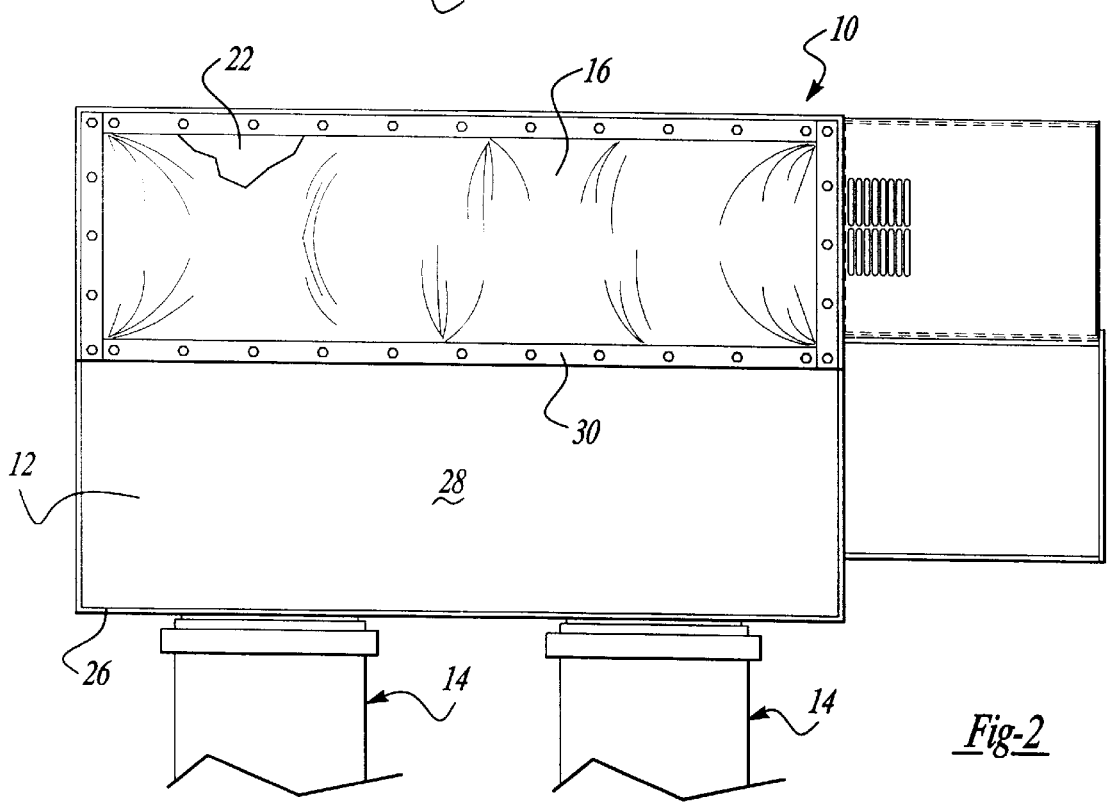
FIG. 2 is a top view of the enclosure shown in FIG. 1.

As shown in FIG. 2, the diaphragm 16 extends the entire width of the enclosure 12 and is secured to the top 28 of the enclosure 12. The top 28 has an opening 32 which is closed by an airtight securement of the diaphragm to the top wall 28 by a structural member 30 which firmly secures the periphery of the diaphragm 16 to the top wall 28 so that the diaphragm 16 communicates with the anaerobic chamber 34 within the enclosure 12.

In the use of the anaerobic enclosure 12, the operator inserts his/her arms into the sleeves 24 and a foot operated sleeve-vacuum system creates an inert atmosphere in the sleeves prior to removing arm port plugs (not shown) in the sleeves 14 and securing the openings 27 against oxygen leaks into the chamber 34. The operators arms are then moved through the openings 27 into the chamber 34 without disturbing the chamber atmosphere. Tactile efficiency is thus improved during subsequent tasks.

The arm port plugs, when in place, allow the sleeves to be changed easily to accommodate correct fit of the latex cuff 22, or replace damaged sleeves 24 without allowing oxygen into the chamber. This design is primarily for microaerophilic.

Figure 3:
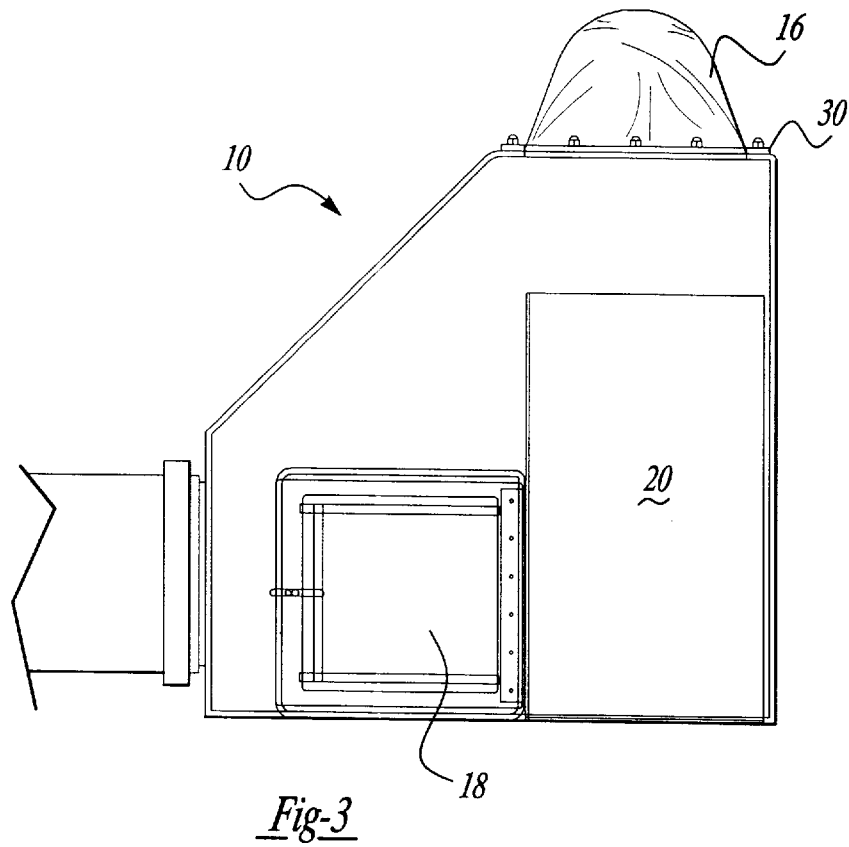
FIG. 3 is an elevational view of one end of the enclosure showing the diaphragm in a bulged condition.

When the desired atmosphere in the chamber 34 is achieved, the diaphragm 16, which is an all-clear plastic sheet that is impervious to oxygen, but will readily wrinkle to accommodate collapse and un-wrinkle when the diaphragm 16 is in its bulged condition shown in FIG. 3.

Figure 4:
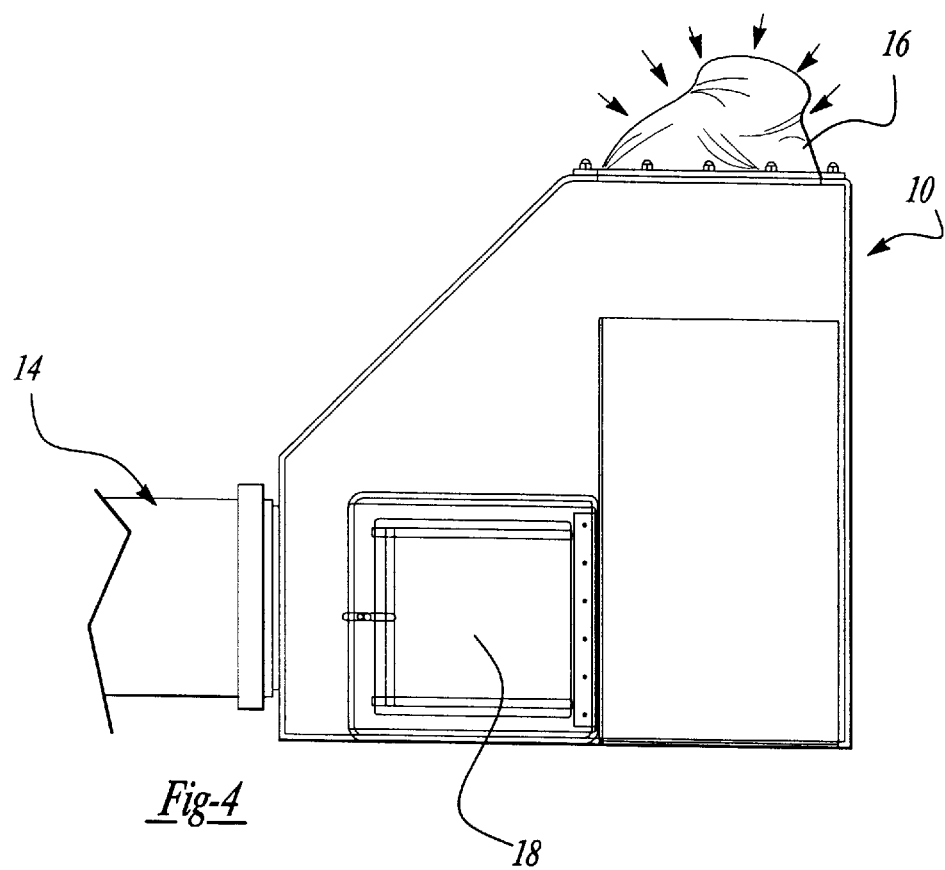
FIG. 4 is an end view like FIG. 3 showing the diaphragm in a collapsed condition.

As shown in FIG. 1, when the operator is handling and inspecting samples in the chamber 34, with his bare hands, the bulged diaphragm is at practically eye-level of the operator. Thus, in the event of a oxygen leakage into the chamber 34, the operator will instantaneously be informed of this fact because the diaphragm 16 would change from its bulged condition shown in FIG. 3 to the collapsed condition shown in FIG. 4. As a result, this simple use of a large diaphragm 16 as arranged and positioned as heretofore explained, enhances the operators ability to more easily use glove-free ability to handle and inspect samples. As is well known in this field, tactile efficiency is improved.

It is to be understood that the invention is not limited to the exact construction illustrated and described above, but that various changes and modifications may be made without departing from the spirit and scope of the invention as defined in the following claims.

What is claimed is:

1. An enclosure defining an anaerobic chamber for confining an anaerobic atmosphere, side-by-side access openings in said enclosure, cuff and sleeve assemblies operatively connected to said enclosure at said openings so that the assemblies are in an airtight relation to said enclosure so as to enable a user of the chamber to insert his/her arms into said cuff and sleeve assemblies in an airtight engagement with the enclosure so that the users hands can be projected into the chamber without allowing oxygen into the chamber thereby offering the user the glove-free ability to handle and inspect samples in the chamber, means forming an opening in said enclosure communicating with said chamber, an expandable diaphragm mounted on said enclosure so as to close said opening thereby providing a continuous visual signal as to the condition of the atmosphere in the chamber, the outward bulging of the diaphragm indicating that oxygen is not leaking into the chamber, and when the diaphragm collapses it is a signal that oxygen is leaking into the chamber.

* * * * *